United States Patent [19]

Ehrenfreund

[11] Patent Number: 4,725,302
[45] Date of Patent: Feb. 16, 1988

[54] SUBSTITUTED PHENYLHYDRAZINES AND PHENYLOXADIAZOLINONES AND PESTICIDAL USAGE THEREOF

[75] Inventor: Josef Ehrenfreund, Allschwil, Switzerland

[73] Assignee: Ciba-Geigy Corporation, Ardsley, N.Y.

[21] Appl. No.: 800,179

[22] Filed: Nov. 20, 1985

[30] Foreign Application Priority Data

Nov. 27, 1984 [CH] Switzerland .................. 5655/84
Nov. 27, 1984 [CH] Switzerland .................. 5656/84
Jul. 18, 1985 [CH] Switzerland .................. 3122/85
Oct. 25, 1985 [CH] Switzerland .................. 4608/85

[51] Int. Cl.⁴ .................. A61K 31/42; C07D 271/10; C07D 307/04; C07D 309/04
[52] U.S. Cl. .................. 71/88; 514/459; 514/460; 514/461; 514/471; 514/473; 514/478; 514/364; 548/144; 549/416; 549/475; 549/495; 564/310; 564/321; 71/92; 71/98; 71/102; 71/111; 71/118
[58] Field of Search .................. 548/144; 564/310; 549/416, 475, 497, 495; 514/364, 459, 460, 473, 461, 471, 478; 71/92, 88, 98, 102, 111, 118

[56] References Cited

U.S. PATENT DOCUMENTS

| 3,846,440 | 11/1974 | Boesch et al. | 548/144 |
| 3,941,798 | 3/1976 | Fort et al. | 548/144 |
| 4,076,824 | 2/1978 | Boesch | 548/144 |
| 4,138,404 | 2/1979 | Fort et al. | 548/144 |
| 4,150,142 | 4/1979 | Boesch | 548/144 |
| 4,174,958 | 11/1979 | Pilgram | 548/144 |
| 4,318,731 | 3/1982 | Kajiokca et al. | 564/310 |
| 4,404,019 | 9/1983 | Uematsu et al. | 564/310 |
| 4,406,910 | 9/1983 | Pilgram et al. | 548/144 |

FOREIGN PATENT DOCUMENTS

| 28039 | 2/1982 | Japan | 564/310 |
| 2093448 | 9/1982 | United Kingdom . | |

OTHER PUBLICATIONS

Ehrenfreund, CA 105-152686c (1986).

Primary Examiner—Donald G. Daus
Assistant Examiner—Cecilia Shen
Attorney, Agent, or Firm—Edward McC. Roberts; Kevin T. Mansfield

[57] ABSTRACT

Phenylhydrazines of the formula I

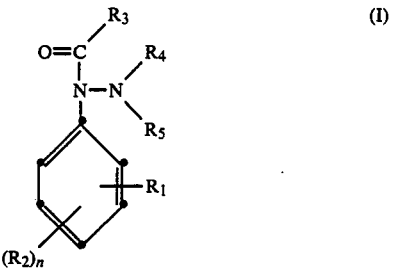

wherein
$R_1$ is —A—R—Z,
A is oxygen, sulfur,

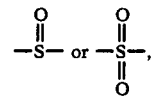

R is $C_1$–$C_6$-alkylene, $C_1$–$C_6$-haloalkyl-$C_1$–$C_6$-alkylene, $C_1$–$C_6$-alkoxy-$C_1$–$C_6$-alkylene or $C_1$–$C_6$-alkylthio-$C_1$–$C_6$-alkylene,
Z is halogen, $C_1$–$C_6$-haloalkyl, $C_1$–$C_6$-alkoxy, $C_1$–$C_6$-alkylthio, $C_1$–$C_6$-alkylsulfinyl or $C_1$–$C_6$-alkylsulfonyl, or
R and Z together are

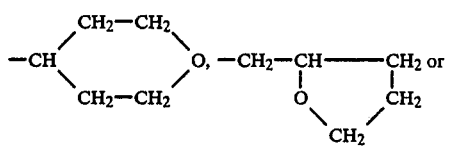

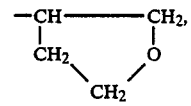

$R_2$ is hydrogen, halogen, $C_1$–$C_6$-alkyl, $C_1$–$C_6$-alkoxy, $C_1$–$C_6$-alkylthio or ($C_1$–$C_6$-alkyl)$_2$amino,
n is a number from 1–4, and $R_2$ can be different when n is one of the numbers 2–4,
$R_3$ is halogen,
$R_4$ is hydrogen,
$R_5$ is —COOR$_6$, or
$R_3$, $R_4$ and $R_5$ together form a bridge member of the formula

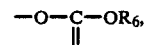

and
$R_6$ is $C_1$–$C_6$-alkyl, $C_2$–$C_6$-alkenyl or $C_2$–$C_6$-alkynyl.

A process for producing these phenylhydrazines and their use for controlling pests are described.

22 Claims, No Drawings

SUBSTITUTED PHENYLHYDRAZINES AND PHENYLOXADIAZOLINONES AND PESTICIDAL USAGE THEREOF

The present invention relates to phenylhydrazines, to processes for producing them, and to their use for controlling pests.

The phenylhydrazines correspond to formula I

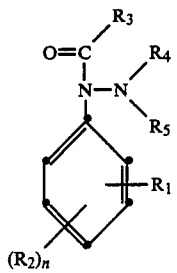

wherein
$R_1$ is —A—R—Z,
A is oxygen, sulfur,

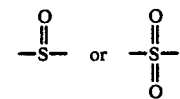

R is $C_1$-$C_6$-alkylene. $C_1$-$C_6$-haloalkyl-$C_1$-$C_6$-alkylene, $C_1$-$C_6$-alkoxy-$C_1$-$C_6$-alkylene or $C_1$-$C_6$-alkylthio-$C_1$-$C_6$-alkylene,
Z is halogen, $C_1$-$C_6$-haloalkyl, $C_1$-$C_6$-alkoxy, $C_1$-$C_6$-alkylthio, $C_1$-$C_6$-alkylsulfinyl or $C_1$-$C_6$-alkylsulfonyl, or
R and Z together are

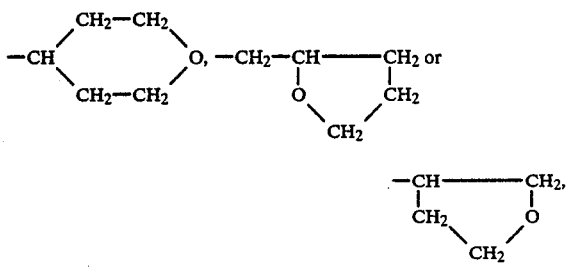

$R_2$ is hydrogen, halogen, $C_1$-$C_6$-alkyl, $C_1$-$C_6$-alkoxy, $C_1$-$C_6$-alkylthio or ($C_1$-$C_6$-alkyl)$_2$amino,
n is a number from 1-4, and $R_2$ can be different when n is one of the numbers 2-4,
$R_3$ is halogen,
$R_4$ is hydrogen,
$R_5$ is —COOR$_6$, or
$R_3$, $R_4$ and $R_5$ together form a bridge member of the formula

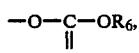

and
$R_6$ is $C_1$-$C_6$-alkyl, $C_2$-$C_6$-alkenyl or $C_2$-$C_6$-alkynyl.

By halogen for R, $R_2$, $R_3$ and Z is meant fluorine, chlorine, bromine or iodine. In the case of $R_3$ it is in particular fluorine or chlorine, but more especially fluorine.

The alkyl, alkoxy, alkylthio, alkylsulfinyl, alkylsulfonyl, alkenyl and alkynyl groups for R, $R_2$, $R_6$ and Z can be straight-chain or branched-chain, and can be unsubstituted or substituted by halogen, $C_1$-$C_6$-alkoxy or $C_1$-$C_6$-alkylthio. Examples of such groups are, inter alia: methyl, methoxy, methylthio, trifluoromethyl, ethyl, ethoxy, pentafluoroalkoxy, propyl, propoxy, propylthio, isopropyl, isopropoxy, isopropylthio, n-butyl, n-butoxy, n-butylthio, n-pentyl, n-pentoxy, n-pentylthio, n-hexyl, n-hexoxy, n-hexylthio and isomers thereof, 2-methylthioethoxy, 2-methoxyethoxy, propenyl or propionyl.

The alkylene groups for R can be straight-chain or branched-chain. Examples of such groups are, inter alia:

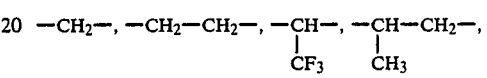

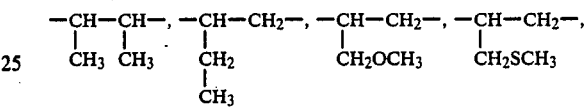

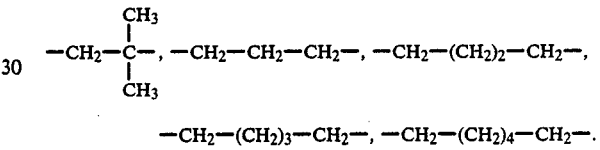

The compounds of the formula I are open-chain phenylhydrazines of the formula

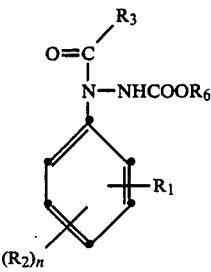

wherein $R_1$, $R_2$, $R_3$, $R_6$ and n have the meanings defined under the formula I; or oxadiazolinones of the formula

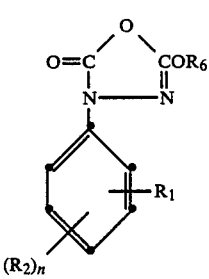

wherein $R_1$, $R_2$, $R_6$ and n have the meanings defined under the formula I.

Preferred compounds are those of the formula Ia wherein $R_1$ is —A—R—Z—,
A is oxygen, sulfur,

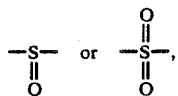

R is $C_2$–$C_6$-alkylene,
Z is halogen, $C_1$–$C_6$-haloalkyl, $C_1$–$C_6$-alkoxy, $C_1$–$C_6$-alkylthio, $C_1$–$C_6$-alkylsulfinyl or $C_1$–$C_6$-alkylsulfonyl; or
R and Z together are

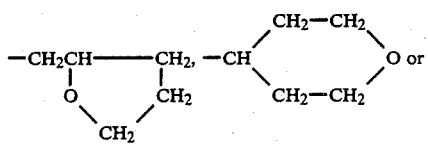

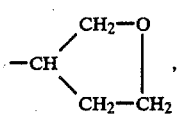

$R_2$ is hydrogen, halogen, $C_1$–$C_6$-alkyl, $C_1$–$C_6$-alkoxy, $C_1$–$C_6$-alkylthio or ($C_1$–$C_6$-alkyl)$_2$amino,
n is a number from 1–4, and $R_2$ can be different when n is one of the numbers 2–4,
$R_3$ is halogen, and
$R_6$ is $C_1$–$C_6$-alkyl, $C_2$–$C_6$-alkenyl or $C_2$–$C_6$-alkynyl;
or compounds of the formula Ib wherein
$R_1$ is —A—R—Z,
A is oxygen, sulfur,

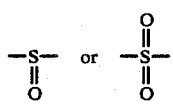

R is $C_2$–$C_6$-alkylene,
Z is halogen, $C_1$–$C_6$-haloalkyl, $C_1$–$C_6$-alkoxy, $C_1$–$C_6$-alkylthio, $C_1$–$C_6$-alkylsulfinyl or $C_1$–$C_6$-alkylsulfonyl; or
R and Z together are

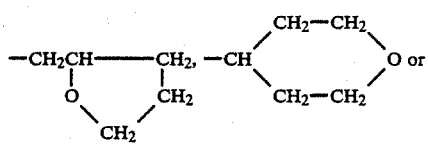

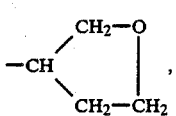

$R_2$ is hydrogen, halogen, $C_1$–$C_6$-alkyl, $C_1$–$C_6$-alkoxy, $C_1$–$C_6$-alkylthio or ($C_1$–$C_6$-alkyl)$_2$amino,
n is a number from 1–4, and $R_2$ can be different when n is one of the numbers 2–4, and
$R_6$ is $C_1$–$C_6$-alkyl, $C_2$–$C_6$-alkenyl or $C_2$–$C_6$-alkynyl;
or compounds of the formula Ib wherein
$R_1$ is —A—R—Z,
A is oxygen, sulfur,

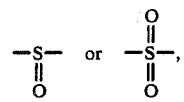

R is $C_2$–$C_6$-alkylene,
Z is halogen, $C_1$–$C_6$-alkoxy, $C_1$–$C_6$-alkylsulfinyl or $C_1$–$C_6$-alkylsulfonyl,
$R_2$ is hydrogen, halogen, $C_1$–$C_6$-alkoxy, $C_1$–$C_6$-alkylthio or ($C_1$–$C_6$-alkyl)$_2$amino,
n is a number from 1–4, and $R_2$ can be different when n is one of the numbers 2–4, and
$R_6$ is $C_1$–$C_6$-alkyl, $C_2$–$C_6$-alkenyl or $C_2$–$C_6$-alkynyl.
Particularly preferred are compounds of the formula Ia
wherein
$R_1$ is —A—R—Z,
A is oxygen or sulfur,
$R_1$ is unsubstituted $C_2$–$C_6$-alkylene,
Z is halogen, $C_1$–$C_6$-alkoxy, $C_1$–$C_6$-alkylthio, $C_1$–$C_6$-alkylsulfinyl or $C_1$–$C_6$-alkylsulfonyl,
$R_2$ is hydrogen, halogen or $C_1$–$C_6$-alkyl,
n is the number 1,
$R_3$ is halogen, and
$R_6$ is methyl;
or compounds of the formula Ia wherein
$R_1$ is —A—R—Z in the 2-position with respect to the group

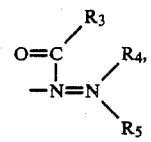

A is oxygen,
R is unsubstituted $C_2$–$C_4$-alkylene,
Z is halogen, $C_1$–$C_4$-alkoxy, $C_1$–$C_4$-alkylthio, $C_1$–$C_4$-alkylsulfinyl or $C_1$–$C_4$-alkylsulfonyl,
$R_2$ is hydrogen, halogen or $C_1$–$C_6$-alkyl,
n is the number 1,
$R_3$ is halogen, and
$R_6$ is methyl;
or compounds of the formula Ib wherein
$R_1$ is —A—R—Z,
A is oxygen or sulfur,
R is $C_2$–$C_6$-alkylene,
Z is halogen, $C_1$–$C_6$-alkoxy, $C_1$–$C_6$-alkylthio, $C_1$–$C_6$-alkylsulfinyl or $C_1$–$C_6$-alkylsulfonyl,
$R_2$ is hydrogen, halogen or $C_1$–$C_6$-alkyl,
n is the number 1, and
$R_6$ is methyl;
or compounds of the formula Ib wherein
$R_1$ is —A—R—Z in the 2-position with respect to the group

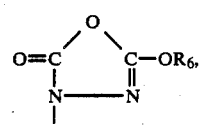

A is oxygen,
R is $C_2$–$C_4$-alkylene,

Z is halogen, $C_1$-$C_4$-alkoxy, $C_1$-$C_4$-alkylthio, $C_1$-$C_4$-alkylsulfinyl or $C_1$-$C_4$-alkylsulfonyl,
$R_2$ is hydrogen, halogen or $C_1$-$C_4$-alkyl,
n is the number 1, and
$R_6$ is methyl.

Examples of compounds of the formula I are, inter alia:

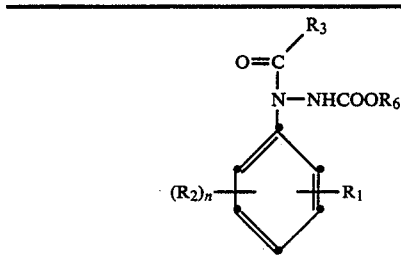

| $R_3$ | $R_1$ | $R_2$ | n | $R_6$ |
|---|---|---|---|---|
| Cl | 2-O(CH$_2$)$_3$SCH$_3$ | H | 1 | CH$_3$ |
| F | 2-OCH$_2$CHOCH$_3$ \| CH$_3$ | H | 1 | C$_2$H$_5$ |
| F | 2-OCH$_2$CF$_3$ | H | 1 | CH$_3$ |
| F | 2-OCHCH$_2$OCH$_3$ \| CH$_3$ | 6-CH$_3$ | 1 | n-C$_4$H$_9$ |
| F | 2-O(CH$_2$)$_2$SCH$_3$ | 5-CH$_3$ | 1 | —CH$_2$CH=CH$_2$ |
| Cl | 2-O(CH$_2$)$_2$SCH$_3$ | 3,5-CH$_3$ | 2 | —CH$_2$C≡CH |
| F | 2-O(CH$_2$)$_2$SCH$_3$ | 3,5-CH$_3$ | 2 | CH$_3$ |
| F | 2-O(CH$_2$)$_2$SCH$_3$ | H | 1 | n-C$_6$H$_{13}$ |
| F | 2-O(CH$_2$)$_2$OCH$_3$ | H | 1 | CH$_3$ |
| Cl | 2-O(CH$_2$)$_2$SCH$_3$ | 4-CH$_3$ | 1 | CH$_3$ |
| F | 2-O(CH$_2$)$_2$SCH$_3$ | 4-CH$_3$ | 1 | C$_2$H$_5$ |
| F | 2-OCH$_2$CHOCH$_3$ \| CF$_3$ | 5-CH$_3$ | 1 | n-C$_4$H$_9$ |
| F | 2-OCH$_2$CHOCH$_3$ \| CH$_3$ | 3,5-CH$_3$ | 2 | n-C$_4$H$_9$ |
| F | 2-OCH$_2$CHOCH$_3$ \| CH$_3$ | 4,5-CH$_3$ | 2 | CH$_3$ |
| F | 2-OCHCH$_2$OCH$_3$ \| CH$_3$ | 4-CH$_3$ | 1 | CH$_3$ |
| F | 2-OCHCH$_2$OCH$_3$ \| CH$_3$ | 3-CH$_3$ | 1 | CH$_3$ |
| Cl | 2-OCHCH$_2$OCH$_3$ \| CH$_3$ | 3,4,5-CH$_3$ | 3 | CH$_3$ |
| Cl | 2-O(CH$_2$)$_2$OCH$_3$ | 3,4,5-CH$_3$ | 3 | CH$_3$ |
| Cl | 2-OCH$_2$—CH—OCH$_3$ \| CH$_3$ | 3,4,5-CH$_3$ | 3 | n-C$_4$H$_9$ |
| F | 2-OCHCH$_2$OCH$_3$ \| CH$_3$ | 4,5-CH$_3$ | 2 | —CH$_2$—CH=CH$_2$ |
| Cl | 2-OCHCH$_2$OCH$_3$ \| CH$_3$ | 5-C$_3$H$_{7(i)}$ | 1 | CH$_3$ |

-continued

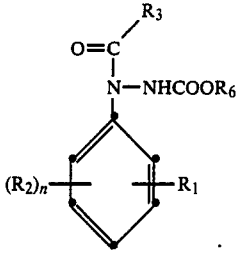

| $R_3$ | $R_1$ | $R_2$ | n | $R_6$ |
|---|---|---|---|---|
| F | 2-OCHCH$_2$OCH$_3$ \| CH$_3$ | 5-C$_3$H$_{7(i)}$ | 1 | CH$_3$ |

| $R_1$ | $R_2$ | n | $R_6$ |
|---|---|---|---|
| 2-O(CH$_2$)$_2$SCH$_3$ | 4-CH$_3$ | 1 | CH$_3$ |
| 2-O(CH$_2$)$_2$SCH$_3$ | 3,5-CH$_3$ | 2 | C$_2$H$_5$ |
| 2-O(CH$_2$)$_2$SO$_2$CH$_3$ | 3,5-CH$_3$ | 2 | CH$_3$ |
| 2-O(CH$_2$)$_2$SO$_2$CH$_3$ | 4-CH$_3$ | 1 | CH$_3$ |
| 2-O(CH$_2$)$_2$SO$_2$CH$_3$ | 3-CH$_3$ | 1 | CH$_3$ |
| 2-O(CH$_2$)$_2$OCH$_3$ | 4-CH$_3$ | 1 | n-C$_4$H$_9$ |
| 2-O(CH$_2$)$_2$OCH$_3$ | 3-CH$_3$ | 1 | —CH$_2$—CH=CH$_2$ |
| 2-O(CH$_2$)$_2$OCH$_3$ | 6-CH$_3$ | 1 | CH$_3$ |
| 2-O(CH$_2$)$_2$OCH$_3$ | 3,4-CH$_3$ | 2 | CH$_3$ |
| 2-O(CH$_2$)$_2$OCH$_3$ | 3,5-CH$_3$ | 2 | CH$_3$ |
| 2-O(CH$_2$)$_2$OCH$_3$ | 4,5-CH$_3$ | 2 | CH$_3$ |
| 2-O(CH$_2$)$_2$OCH$_3$ | 4,6-CH$_3$ | 2 | CH$_3$ |
| 2-OCHCH$_2$OCH$_3$ \| CH$_3$ | 3,4-CH$_3$ | 2 | CH$_3$ |
| 2-OCHCH$_2$OCH$_3$ \| CH$_3$ | 4,5-CH$_3$ | 2 | CH$_3$ |
| 2-OCHCH$_2$OCH$_3$ \| CH$_3$ | 4,6-CH$_3$ | 2 | CH$_3$ |
| 2-OCHCH$_2$OCH$_3$ \| CH$_3$ | 3-CH$_3$ | 1 | C$_2$H$_5$ |
| 2-OCHCH$_2$OCH$_3$ \| CH$_3$ | 4-CH$_3$ | 1 | n-C$_4$H$_9$ |
| 2-O(CH$_2$)$_2$SCH$_3$ | 3-CH$_3$ | 1 | n-C$_6$H$_{13}$ |
| 2-OCHCH$_2$OCH$_3$ \| CH$_3$ | 3,4,5-CH$_3$ | 3 | CH$_3$ |
| 2-O(CH$_2$)$_2$OCH$_3$ | 3,4-CH$_3$ | 2 | CH$_3$ |
| 2-O(CH$_2$)$_2$SCH$_3$ | 3,4-CH$_3$ | 2 | CH$_3$ |
| 2-O(CH$_2$)$_2$SCH$_3$ | 4,5-CH$_3$ | 2 | CH$_3$ |
| 2-O(CH$_2$)$_2$SCH$_3$ | 4,6-CH$_3$ | 2 | CH$_3$ |
| 2-O(CH$_2$)$_2$SO$_2$CH$_3$ | 3,4-CH$_3$ | 2 | CH$_3$ |
| 2-O(CH$_2$)$_2$SO$_2$CH$_3$ | 4,5-CH$_3$ | 2 | CH$_3$ |

-continued

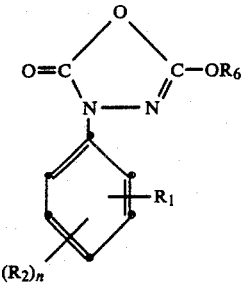

| $R_1$ | $R_2$ | n | $R_6$ |
|---|---|---|---|
| $-O(CH_2)_2SO_2CH_3$ | 4,6-$CH_3$ | 2 | $CH_3$ |
| 2-$O(CH_2)_2SO_2CH_3$ | 6-$CH_3$ | 1 | $-CH_2-C{\equiv}CH$ |
| 2-$O(CH_2)_2SCH_3$ | 6-$CH_3$ | 1 | $-CH_2-CH{=}CH_2$ |
| 2-$OCH_2CH(CF_3)OCH_3$ | 5-$CH_3$ | 1 | $n$-$C_4H_9$ |
| 2-$OCH_2CH(CH_3)OCH_3$ | 4-$CH_3$ | 1 | $n$-$C_3H_7$ |
| 2-$OCH_2CH(CH_3)OCH_3$ | 5-$CH_3$ | 1 | $n$-$C_3H_7$ |
| 2-$OCH_2CH(CH_3)OCH_3$ | 6-$CH_3$ | 1 | $n$-$C_3H_7$ |
| 2-$OCH_2CH(CH_3)OCH_3$ | 3,4-$CH_3$ | 2 | $i$-$C_3H_7$ |
| 2-$OCH_2CH(CH_3)OCH_3$ | 3,5-$CH_3$ | 2 | $i$-$C_3H_7$ |
| 2-$OCH_2CH(CH_3)OCH_3$ | 4,5-$CH_3$ | 2 | $i$-$C_3H_7$ |
| 2-$OCH_2CH(CH_3)OCH_3$ | 4,6-$CH_3$ | 2 | $i$-$C_3H_7$ |
| 2-$OCH_2CH(CH_3)OCH_3$ | 3,4-$CH_3$ | 2 | $CH_3$ |
| 2-$O(CH_2)_3OCH_3$ | H | 1 | $CH_3$ |
| 2-$O(CH_2)_3SCH_3$ | H | 1 | $n$-$C_4H_9$ |
| 2-$OC(CH_3)_2CH_2OCH_3$ | H | 1 | $CH_3$ |
| 2-$OCH_2C(CH_3)(C_2H_5)OCH_3$ | H | 1 | $C_2H_5$ |
| 2-$OCH(CH_3)CH(CH_3)OCH_3$ | H | 1 | $CH_3$ |
| 2-$OCH(CH_3)CH(CH_3)OCH_3$ | H | 1 | $C_2H_5$ |
| 2-$OCH(CH_3)CH(CH_3)OCH_3$ | 5-$CH_3$ | 1 | $n$-$C_3H_7$ |

-continued

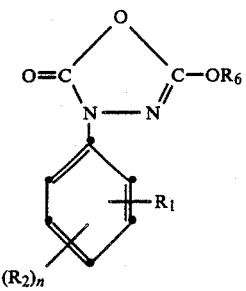

| $R_1$ | $R_2$ | n | $R_6$ |
|---|---|---|---|
| 2-$OCH_2CH(CH_3)SCH_3$ | H | 1 | $i$-$C_3H_7$ |
| 2-$OCH_2C(CH_3)_2SCH_3$ | H | 1 | $i$-$C_3H_7$ |
| 2-$O(CH_2)_3SO_2CH_3$ | H | 1 | $-CH_2-CH{=}CH_2$ |
| 2-$OCH(CH_3)CH_2-OCH_3$ | 5-$C_2H_5$ | 1 | $CH_3$ |
| 2-$OCH(CH_3)CH_2OCH_3$ | 5-$C_3H_{7(i)}$ | 1 | $CH_3$ |
| 2-$OCH(CH_3)CH_2OCH_3$ | 5-$C_4H_{9(t)}$ | 1 | $CH_3$ |
| 2-$OCH_2CF_3$ | 5-$CH_3$ | 2 | $CH_3$ |

The compounds of the formula I can be obtained, using methods known per se, by producing in a first step, by phosgenation or fluorphosgenation, compounds of the formula I wherein $R_5$ is $-COOR_6$, X is halogen and Y is hydrogen, and subsequently cyclising these open-chain hydrazines by means of a base to compounds of the formula I wherein $R_3$, $R_4$ and $R_5$ together are $$-O-\underset{OR_6}{C}{=}:$$

$$\underset{(II)}{\underset{(R_2)_n}{\text{Ar}}}{\text{NH--NH--COOR}_6}\ \ + \ \text{CO}(R_3)_2 \longrightarrow$$
(III)

-continued

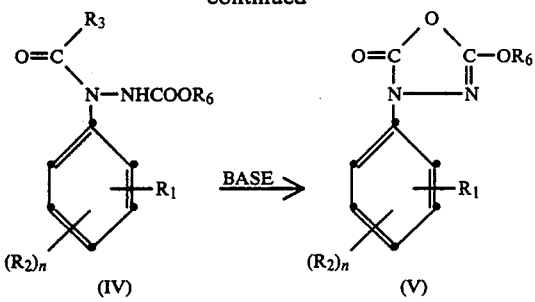

In the formulae II–V, the symbols $R_1$, $R_2$, $R_3$, $R_6$ and n have the meanings defined under the formula I.

Suitable bases for the second process step are in particular organic bases, such as trialkylamines, for example triethylamine or ethyldiisopropylamine, pyridine, dialkylanilines or cyclic amidine bases.

Both process steps are performed at a reaction temperature of between $-10°$ and $120°$ C., usually between $20°$ and $80°$ C., under normal or elevated pressure and preferably in an inert solvent or diluent. Suitable solvents or diluents are for example: ethers and ethereal compounds, such as diethyl ether, dipropyl ether, dioxane, dimethoxyethane and tetrahydrofuran; amides, such as N,N-dialkylated carboxylic acid amides; aliphatic, aromatic as well as halogenated hydrocarbons, especially benzene, toluene, xylenes, chloroform and chlorobenzene; nitriles, such as acetonitrile; dimethyl sulfoxide and ketones, such as acetone and methyl ethyl ketone, and also alcohols (only in the cyclisation step), for example methanol, ethanol, propyl alcohol, and so forth, and esters, for example ethyl acetate.

The starting materials of the formula II can be produced by methods analogous to known methods (cp. Example 1).

The compounds of the formula I which contain S in its oxidised form, that is, as

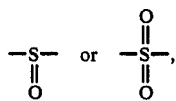

can be obtained also by oxidation of the corresponding compounds I in which the sulfur is present as sulfide. Oxidation reactions of this kind are well known in the literature, and are performed for example by means of hydrogen peroxide, alkali periodates or organic peracids, such as perbenzoic acid, 3-chloroperbenzoic acid or peracetic acid. Further reagents suitable for such reactions are mentioned in the monograph L.F. Fieser and M. Fieser, Reagents for Organic Synthesis, Vol. 1–10 (J. Wiley and Sons, Inc.).

Compounds of the formula I in which $R_4$ is hydrogen, $R_5$ is $-COOR_6$ ad $R_3$ is fluorine can be produced also from the corresponding compounds of the formula I in which $R_3$ is chlorine; for example by reaction with alkali fluorides in suitable solvents, optionally with the addition of crown compounds or phase-transfer catalysts, or by reaction with anhydrous hydrofluoric acid, antimony fluorides or other suitable reagents (Angew. Chemie 89, 797 (1977)).

The compounds of the formula I are suitable for controlling various pests on animals and plants as well as in the soil. They can thus be used for controlling insects, for example of the orders: Lepidoptera, Coleoptera, Homoptera, Heterooptera, Diptera, Thysanoptera, Orthoptera, Anoplura, Siphonaptera, Mallophaga, Thysanura, Isoptera, Psocoptera and Hymenoptera, and also mites and ticks of the order Acarina.

In particular, compounds of the formula I are suitable for controlling insects that damage plants in crops of ornamental plants and productive plants, especially in cotton and rice crops (for example against Spodoptera littoralis, Heliothis virescens, Nephothettix cincticeps, Chilo suppressalis and Laodelphax striatellus) and in vegetable and fruit crops (for example against Leptinotarsa decemlineata, Myzus persicae, Laspeyresia pomonella and Adoxophyes reticulana), and also for controlling soil insects (for example Aulacophora femoralis, Chortophila brassicae, Diabrotica balteata, Pachnoda savignyi and Scotia ypsilon). To be particularly emphasised is the high level of systemic activity, which is effective especially for the control of sucking insects and phytopathogenic fungi.

Active substances of the formula I exhibit also a very favourable action against flies, for example Musca domestica, as well as against mosquito larvae. In addition, the compounds of the formula I have good nematocidal properties; they are also distinguished by a broad ovidical and ovilarvidical action, and have moreover a valuable action against ectoparasitic mites and ticks, for example of the families: Ixodidae, Argasidae and Dermanyssidae.

The compounds of the formula I are effective also against phytopathogenic fungi. Thus the compounds of the formula I have a good action against phytopathogenic fungi belonging to the following classes: Ascomycetes (for example: Erysiphaceae, Fusarium and Helminthosporium); Basidiomycetes, such as: Puccinia, Rhizoctonia, Tilletia, or Hemileia; Fungi imperfecti (for example Cercospora, Botrytis or Septoria); and Phycomycetes, such as Phytophthora.

The compounds of the formula I can advantageously be used as dressing agents for the treatment of seed and stored provisions (fruit, tubers and grain) and also plant cuttings, and for seed furrow application for protection against fungus infections and against insects and members of the order Acarina, as well as against phytopathogenic fungi and insects present in the soil.

The acaricidal and insecticidal action can be substantially broadened and adapted to suit the given circumstances by the addition of other insecticides and/or acaricides. Suitable additives are for example: organic phosphorus compounds, nitrophenols and derivatives thereof, formamidines, ureas, other pyrethrin-like compounds, as well as carbamates and chlorinated hydrocarbons.

Compounds of the formula I are combined particularly advantageously also with substances which have a synergistic or intensifying effect. Examples of compounds of this type are, inter alia: piperonylbutoxide, propynyl ethers, propynyl oximes, propynl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-octylsulfinyl)-propyl) benzene.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ethyl acetate, propylmyristate and propylpalmitate, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite, and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included amongst these are also the salts of sulfuric acid esters and of sulfonic acids of fatty alcohol ethylene oxide adducts. The sulfonated benzimidazole derivatives preferably contain 2 sulfonic acid groups and a fatty acid group having 8–22 C atoms.

Alkylarylsulfonates are for example the Na, Ca or triethanolamine salts of dodecylbenzenesulfonic acid, of dibutylnaphthalenesulfonic acid, or of a naphthalenesulfonic acid-formaldehyde condensation product. Also suitable are corresponding phosphates, for example salts of the phosphoric ester of a p-nonylphenol-(4–14)-ethylene oxide adduct, and phospholipids.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, castor oil thioxylate, polypropylene/-polyethylenoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications: "Mc Cutcheon's Detergents and Emulsifiers Annual", MC Publishing Corp., Ridgewood, N.J., 1979; and Dr. Helmut Stache "Tensid Taschenbuch", Carl Hanser Verlag, Munich/Vienna, 1981.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25%, of a tenside.

Whereas commercial products are preferably in the form of concentrated compositions, the preparations employed by the end-user are as a rule diluted.

The compositions can also contain further additives such as stabilisers, antifoam agents, viscosity regulators, binders and adhesives, as well as fertilisers or other active ingredients for obtaining special effects.

PRODUCTION EXAMPLE 1

Production of the compound No. 1.1 of the formula

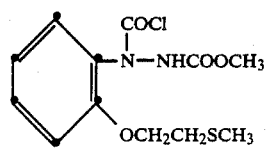

(a) Production of 2-(2-methylthioethoxy)-nitrobenzene 16.3 g of 2-hydroxyethylmethyl sulfide are added dropwise at 20°-25° C. to 8.5 g of a 55% NaH suspension in 150 ml of absolute tetrahydrofuran. The mixture is stirred for 1 hour at 20° C. and for 20 minutes at 40° C., and 25 g of 1-fluoro-2-nitrobenzene are subsequently added at 20° C. After the suspension has been stirred for 10 hours at 20° C., the tetrahydrofuran is distilled off in vacuo. Water is added to the residue, and extraction is repeatedly performed with ether. There is thus obtained an oil which can be used without further purification for the following hydrogenation stage.

(b) Production of 2-(2-methylthioethoxy)-aniline 33.9 g of he oil obtained under (a) are hydrogenated in 100 ml of absolute tetrahydrofuran, with the addition of 13.6 g of Raney nickel, under normal pressure (hydrogen absorption=10.6 liters). After the catalyst has been filtered off, the filtrate is concentrated by evaporation, and then purified by means of chromatography (silica gel; hexane/ethyl acetate as eluant).

There are obtained 27.4 g of oil, which can be used directly for the following reaction.

(c) Production of 2-(2-methylthioethoxy)-phenylhydrazine 27.4 g of the aniline obtained under (b) are placed into 45 ml of glacial acetic acid and, with ice cooling, a mixture of 37 ml of concentrated HCl and 75 ml of H$_2$O is added. The formed suspension is diazotised at 0°-5° C. with 10.3 g of NaNO$_2$ in 22 ml of water. The diazonium solution is subsequently stirred at 0° C. for 10 minutes, and a solution of 80.7 g of SnCl$_2$.2H$_2$O in 112 ml of concentrated HCl is then quickly added with cooling. After 4 hours, water is added to the reaction mixture, and extraction is repeatedly performed with ether. The aqueous phase is afterwards rendered alkaline with a 10% aqueous sodium hydroxide solution, and extracted three times with ether. After customary further processing of the ether phases, there is obtained the compound of the formula

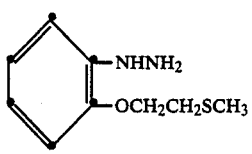

having a melting point of 72.5°-74.5° C.

(d) Production of 2-[2-(methylthioethoxy)-phenyl]-hydrazinecarboxylic acid methyl ester 5.6 ml of chloroformic acid methyl ester are added dropwise at 0° C. to 14.4 g of 2-(2-methylthioethoxy)-phenylhydrazine in 100 ml of tetrahydrofuran and 14 g of N-ethyldiisopropylamine. The reaction mixture is stirred at 20° C. for 2 hours; H$_2$O is then added, and the mixture is repeatedly extracted with ethyl acetate. After customary further processing, a solid is obtained, and this is recrystallised from alcohol to thus yield the compond of the formula

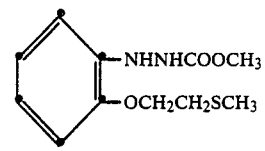

having a melting point of 92°-94° C.

(e) Production of 2-(chlorocarbonyl)-2-[2-(2-methylthioethoxy)-phenyl]-hydrazinecarboxylic acid methyl ester 80 ml of a 20% solution of phosgene in toluene are added at 20° C. to 14.1 g of 2-[2-(2-methylthioethoxy)-phenyl]-hydrazinecarboxylic acid methyl ester in 130 ml of toluene. The reaction mixture is subsequently heated for 3 hours at 90° C., and the solvent is then removed. Recrystallisation of the residue in ethyl alcohol yields the compound No. 1.1 of the formula

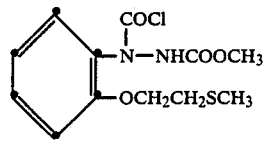

having a melting point of 55°-57° C.

The following compounds are produced in an analogous manner:

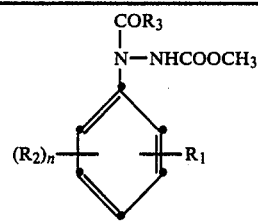

| No. | R$_3$ | R$_1$ | R$_2$ | n | Physical data |
|---|---|---|---|---|---|
| 1.2 | Cl | 2-OCH$_2$CH$_2$Cl | H | 1 | NMR (CDCl$_3$): (60 Mhz) $\delta = 3.35$ s (3H) (OCH$_3$) $\delta = 3.7$ s (3H) (COOCH$_3$) superimposed by $\delta = 3.4$–3.8 (m 2H, —CH$_2$—CH$_2$—) $\delta = 3.9$–4.3 m (2H) |

-continued

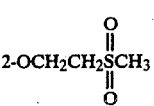

| No. | R₃ | R₁ | R₂ | n | Physical data |
|---|---|---|---|---|---|
| | | | | | (—CH₂—CH₂—) |
| | | | | | δ = 6.7–7.65 m (4H) |
| | | | | | (phenyl protons) |
| | | | | | δ = 8.7 (1H, breit) NH |
| 1.3 | Cl | 2-OCH₂CH₂OCH₃ | H | 1 | NMR (CDCl₃): (60 Mhz) |
| | | | | | δ = 3.7 s (H) (—COOCH₃) |
| | | | | | partially superimposed by |
| | | | | | δ = 3.6–4.0 m (2H) |
| | | | | | (—CH₂CH₂—) |
| | | | | | δ = 4.25 t (2H) |
| | | | | | (—CH₂—CH₂—) |
| | | | | | δ = 6.8–8.0 m (5H) |
| | | | | | (phenyl protons + NH) |
| 1.4 | Cl | 2-OCH₂CH₂S(O)₂CH₃  | H | 1 | m.p.: 128–130° C. |
| 1.5 | Cl | 2-OCH₂CH₂SCH₂CH₃ | H | 1 | m.p.: 75–77° C. |
| 1.6 | Cl | 2-OCH(CH₃)CH₂OCH₃ 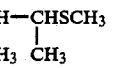 | H | 1 | MS: m/e = 316/318 |
| 1.7 | Cl | 2-OCH₂CH₂F | H | 1 | m.p.: 74–75° C. |
| 1.8 | Cl | 4-OCH₂CH₂SCH₃ | H | 1 | m.p.: 94–96° C. |
| 1.9 | Cl | 2-OCH₂CH₂CH₂SCH₃ | H | 1 | MS: m/e = 332/334 |
| 1.10 | Cl | 2-OCH(CH₃)—CH(CH₃)SCH₃  | H | 1 | MS: m/e = 346/348 |
| 1.11 | Cl | 2-OCH₂CH₂CH₂OCH₂CH₃ | H | 1 | MS: m/e = 330/332 |
| 1.12 | Cl | 2-OCH₂CH₂OCH₂CH₃ | H | 1 | MS: m/e = 316/318 |
| 1.13 | F | 2-OCH(CH₃)CH₂OCH₃  | H | 1 | MS: m/e = 300 |
| 1.14 | F | 2-OCH₂CH(CH₃)OCH₃ 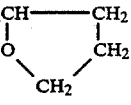 | H | 1 | MS: m/e = 300 |
| 1.15 | Cl | 2-OCH₂CH(OCH₂CH₂CH₂) 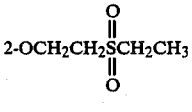 | H | 1 | MS: m/e = 328 |
| 1.16 | Cl | 2-OCH₂CH₂S(O)₂CH₂CH₃ 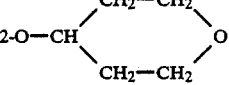 | H | 1 | m.p.: 101–104° C. |
| 1.17 | Cl | 2-O-CH(dioxane)  | H | 1 | m.p.: 139–140° C. |
| 1.18 | Cl | 2-OCH(CH₃)CH₂SCH₃ | H | 1 | m.p.: 139–140° C. |
| 1.19 | F | 2-OCH(dioxane) 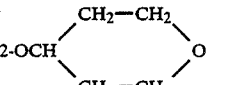 | H | 1 | m.p.: 102–104° C. |

-continued

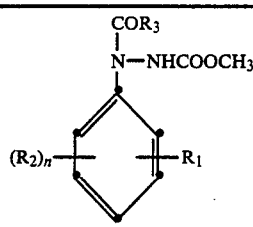

| No. | R₃ | R₁ | R₂ | n | Physical data |
|---|---|---|---|---|---|
| 1.20 | Cl | 2-O—CH—(CH₂)₂ / CH₂—O | H | 1 | m.p.: 105–107.5° C. |
| 1.21 | Cl | 2-O(CH₂)₂CHOCH₃ / CH₃ | H | 1 | MS: m/e 330/332 |
| 1.22 | Cl | 2-O(CH₂)₂OCH₃ | 5-CH₃ | 1 | m.p.: 48–52° C. |
| 1.23 | Cl | 2-OCHCH₂OCH₃ / CH₃ | 5-CH₃ | 1 | m.p.: 73–75° C. |
| 1.24 | F | 2-OCHCH₂OCH₃ / CH₃ | 5-CH₃ | 1 | m.p.: 63–67° C. |
| 1.25 | Cl | 2-O(CH₂)₂SCH₃ | 5-CH₃ | 1 | m.p.: 110–111° C. |
| 1.26 | F | 2-O(CH₂)₂OCH₃ | 5-CH₃ | 1 | m.p.: 71–73° C. |
| 1.27 | Cl | 2-OCH—CH₂OCH₃ / CH₃ | 6-CH₃ | 1 | m.p.: 83–85° C. |
| 1.28 | Cl | 2-OCHCH₂OCH₃ / CH₃ | 3,5-CH₃ | 2 | m.p.: 83–86° C. |
| 1.29 | Cl | 2-OCH₂CHOCH₃ / CH₃ | H | 1 | MS: m/e 316/318 |
| 1.30 | F | 2-OCHCH₂OCH₃ / CH₃ | 3,5-CH₃ | 2 | m.p.: 83–85° C. |
| 1.31 | Cl | 2-OCHCH₂OCH₃ / CH₂OCH₃ | H | 1 | MS: m/e = 346/348 |
| 1.32 | F | 2-OCHCH₂OCH₃ / CH₂OCH₃ | H | 1 | $n_D^{23°} = 1.4962$ |
| 1.33 | F | 2-O—CH——CH₂ / CH₂  CH₂ \ O | H | 1 | m.p.: 90–92° C. |

Production of the compound No. 2.1 of the formula

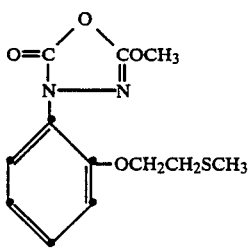

5 ml of triethylamine are added at 20° C. to 5.8 g of 2-(chlorocarbonyl)-2-[2-(methylthioethoxy)-phenyl]-hydrazinecarboxylic acid methyl ester (compound No. 1.1) suspended in 45 ml of methanol. After being stirred for 5 hours at 20° C., the reaction mixture is diluted with water and extracted with ether. The organic phase is separated, washed with water and with a diluted sodium chloride solution, filtered, dried over magnesium sulfate and concentrated by evaporation. The product is chromatographed on silica gel, with toluene/ethyl acetate (95:5) as the eluant, to thus obtain the title product No. 2.1 having a melting point of 52°–53° C.

The following compounds are produced in an analogous manner:

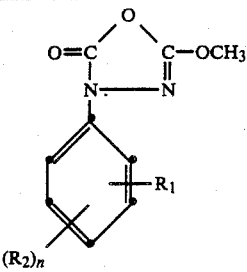

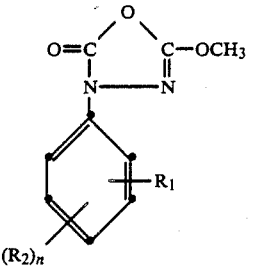

| No. | R$_1$ | R$_2$ | n | Physical data |
|---|---|---|---|---|
| 2.2 | 2-OCH$_2$CH$_2$OCH$_3$ | H | 1 | $n_D^{21°}$ = 1.5260 |
| 2.3 | 2-OCH$_2$CH$_2$Cl | H | 1 | m.p.: 75–78.5° C. |
| 2.4 | 2-SCH$_2$CH$_2$OCH$_3$ | H | 1 | $n_D^{25}$ = 1.560 |
| 2.5 | 2-OCH$_2$CH$_2$SCH$_3$ | H | 1 | m.p.: 73–75° C. |
| 2.6 | 2-OCH$_2$CH$_2$SCH$_2$CH$_3$ | H | 1 | m.p.: 41–43° C. |
| 2.7 | 2-OCHCH$_2$OCH$_3$ \| CH$_3$ | H | 1 | $n_D^{22°}$ = 1.5177 |
| 2.8 | 2-OCH$_2$CH$_2$F | H | 1 | m.p.: 55–57° C. |
| 2.9 | 2-OCH$_2$CH$_2$SOCH$_3$ | H | 1 | m.p.: 119–121° C. |
| 2.10 | 2-OCH$_2$CH$_2$SO$_2$H$_3$ | H | 1 | m.p.: 105–107° C. |
| 2.11 | 2-OCH$_2$CH$_2$OCH$_2$CH$_3$ | H | 1 | m.p.: 44–46° C. |
| 2.12 | 2-OCH$_2$CH$_2$CH$_2$OCH$_2$CH$_3$ | H | 1 | $n_D^{21°}$ = 1.5152 |
| 2.13 | 2-OCH$_2$—CH—CH$_2$ O—CH$_2$—CH$_2$ (epoxide/ring) | H | 1 | MS: m/e = 292 |
| 2.14 | 2-OCH$_2$CH$_2$SO$_2$CH$_2$CH$_3$ | H | 1 | m.p.: 89–91° C. |
| 2.15 | 2-O—CH(CH$_2$—CH$_2$)$_2$O (dioxane) | H | 1 | MS: m/e = 292 |
| 2.16 | 2-OCHCH$_2$SO$_2$CH$_3$ \| CH$_3$ | H | 1 | m.p.: 134–136° C. |
| 2.17 | 2-OCHCH$_2$SCH$_3$ \| CH$_3$ | H | 1 | $n_D^{24°}$ = 1.5459 |
| 2.18 | 2-OCH—CHSCH$_3$ \| \| CH$_3$ CH$_3$ | H | 1 | MS: m/e = 280 |
| 2.19 | 2-O(CH$_2$)$_2$CHOCH$_3$ \| CH$_3$ | H | 1 | $n_D^{23°}$ = 1.5156 |
| 2.20 | 2-O(CH$_2$)$_2$OCH$_3$ | 5-CH$_3$ | 1 | $n_D^{23°}$ = 1.5232 |
| 2.21 | 2-OCHCH$_2$OCH$_3$ \| CH$_3$ | 5-CH$_3$ | 1 | $n_D^{23°}$ = 1.5171 |
| 2.22 | 2-O(CH$_2$)$_2$CHOCH$_3$ \| CH$_3$ | H | 1 | $n_D^{23°}$ = 1.5156 |
| 2.23 | 2-O(CH$_2$)$_2$SCH$_3$ | 5-CH$_3$ | 1 | $n_D^{23°}$ = 1.5520 |
| 2.24 | 2-OCH$_2$CHOCH$_3$ \| CH$_3$ | H | 1 | $n_D^{23°}$ = 1.5189 |
| 2.25 | 2-OCHCH$_2$OCH$_3$ \| CH$_3$ | 3,5-CH$_3$ | 2 | $n_D^{24°}$ = 1.5160 |
| 2.26 | 2-O(CH$_2$)$_2$SO$_2$CH$_3$ | 5-CH$_3$ | 1 | m.p.: 134–136° C. |
| 2.27 | 2-OCHCH$_2$OCH$_3$ \| CH$_3$ | 6-CH$_3$ | 1 | $n_D^{23°}$ = 1.5131 |
| 2.28 | 2-OCHCH$_2$OCH$_3$ \| CH$_2$OCH$_3$ | H | 1 | m.p.: 72–73° C. |
| 2.29 | 2-OCH$_2$CF$_3$ | H | 1 | m.p.: 57–59° C. |

EXAMPLE 2

Formulation Examples for active ingredients according to Production Example 1 (%=percent by weight)

| 2.1 Emulsion concentrates | (a) | (b) | (c) | (d) |
|---|---|---|---|---|
| active ingredient according to Production Example 1 | 10% | 25% | 40% | 50% |
| calcium dodecylbenzenesulfonate | — | 5% | 8% | 6% |
| castor oil-polyethylene glycol ether (36 mols of ethylene oxide) | — | 5% | — | — |
| tributylphenol-polyethylene glycol ether (30 mols of ethylene oxide) | — | — | 12% | 4% |
| castor oil thioxylate | 25% | — | — | — |
| cyclohexanone | — | — | 15% | 20% |
| butanol | 15% | — | — | — |
| xylene mixture | — | 65% | 25% | 20% |
| ethyl acetate | 50% | — | — | — |

Emulsions of any required concentration can be produced from concentrates of this type by dilution with water.

| 2.2 Solutions | (a) | (b) |
|---|---|---|
| active ingredient according to Production Example 1 | 10% | 5% |
| ethylene glycol-monomethyl ether | — | — |
| polyethylene glycol (M.W. 400) | 70% | — |
| N—methyl-2-pyrrolidone | 20% | — |
| epoxidised coconut oil | — | 1% |

| 2.2 Solutions | (a) | (b) |
|---|---|---|
| ligroin (boiling limits 160–190° C.) | — | 94% |

These solutions are suitable for application in the form of very small drops.

| 2.3 Granulates | (a) | (b) |
|---|---|---|
| active ingredient according to Production Example 1 | 5% | 10% |
| kaolin | 94% | — |
| highly dispersed silicic acid | 1% | — |
| attapulgite | — | 90% |

The active ingredient is dissolved in methylene chloride; the solution is then sprayed onto the carrier, and the solvent is subsequently evaporated off in vacuo.

| 2.4. Dusts | (a) | (b) | (c) | (d) |
|---|---|---|---|---|
| active ingredient according to Production Example 1 | 2% | 5% | 5% | 8% |
| highly dispersed silicic acid | 1% | 5% | — | — |
| talcum | 97% | — | 95% | — |
| kaolin | — | 90% | — | 92% |

Dusts ready for use are obtained by the intimate mixing together of the carriers with the active ingredient.

| 2.5. Wettable powders | (a) | (b) | (c) |
|---|---|---|---|
| active ingredient according to Production Example 1 | 20% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 67% | 27% | — |

The active ingredient is well mixed with the additives and the mixture is thoroughly ground in a suitable mill. Wettable powders which can be diluted with water to give suspensions of the required concentration are obtained.

| 2.6. Extruder granulate | |
|---|---|
| active ingredient according to Production Example 1 | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded and then dried in a stream of air.

| 2.7. Coated granulate | |
|---|---|
| active ingredient according to Production Example 1 | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granulates are obtained in this manner.

| 2.8. Suspension concentrate | |
|---|---|
| active ingredient according to Production Example 1 | 40% |
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentration required.

EXAMPLE 3

Biological Examples for active ingredients according to Production Example 1

3.1 Insecticidal stomach-poison action: *Spodoptera littoralis*

Cotton plants are sprayed with a test solution containing 400 ppm of the compound to be tested. After the drying of the coating, larvae of *Spodoptera littoralis* ($L_3$ stage) are settled onto the plants. Two plants are used per test compound, and an evaluation of the mortality rate achieved is made after 2, 4, 24, 48 and 72 hours. The test is carried out at 28° C. with 60% relative humidity.

Compounds according to Example 1 are 80–100% effective against larvae of *Spodoptera littoralis* in the above test.

3.2. Action against *Lucilia sericata*

One ml of an aqueous preparation containing 0.1% of active ingredient is added to 9 ml of a nutrient medium. There are then introduced into the nutrient medium about 30 freshly hatched *Lucilia sericata* larvae. The insecticidal action is assessed after 48 and 96 hours by ascertaining the mortality rate.

Compounds of the formula I according to Example 1 are 80–100% effective in this test against *Lucilia sericata*.

3.3 Action against *Aedes aegypti*

Sufficient of a 0.1% acetonic solution of the active ingredient is transferred by pipette to the surface of 150 ml of water in a container to obtain a concentration of 12.5 ppm. After the acetone has been evaporated off, 30 to 40 two-day-old Aëdes larvae are placed into the container, and the % mortality rate is assessed after 2 and 7 days (number of larvae unable to float).

Compounds according to Example 1 exhibit a 100% action (mortality) in the above test.

3.4. Ovidical action against *Heliothis virescens*

Appropriate proportions of a wettable, pulverulent formulation containing 25% by weight of the active ingredient to be tested are in each case mixed with the amount of water required to obtain aqueous emulsions having concentrations of active ingredient of 400 to 12.5 ppm. One-day-old clusters of eggs of Heliothis on Cellophan ® are immersed in these active-ingredient emulsions for three minutes, and are then filtered off under suction on round filters. The egg clusters treated in this manner are laid out in Petri dishes and stored in darkness. After 6 to 8 days, the hatching rate compared with that of untreated control specimens is determined. The concentration of active ingredient required to effect a 100% mortality rate is taken as a basis for the evaluation.

Compounds according to Example 1 are 100% effective (100% motality rate) at a concentration of 12.5 ppm in this test.

3.5. Action against acarids which damage plants: *Tetranychus urticae* (OP-sensitive) and *Tetranychus cinnabarinus* (OP-tolerant)

The primary leaves of *Phaseolus vulgaris* plants are infested, 16 hours before the test for acaricidal action, with an infested piece of leaf from a mass culture of *Tetranychus urticae* (OP-sensitive) and *Tetranychus cinnabarinus* (OP-tolerant), respectively [tolerance is with respect to diazinon compatibility]. The infested plants treated in this manner are sprayed dripping wet with a test solution containing 400 ppm of the compound to be tested. After 24 hours and again after 7 days, an assessment is made of the imagines and larvae (all mobile stages), of living and of dead individuals. One plant is used per concentration and per test species. The plants stand during the course of the test in greenhouse compartments at 25° C.

Compounds according to Example 1 exhibit in this test an 80–100% action against *Tetranychus urticae* and *Tetranychus cinnabarinus*.

3.6. Insecticidal contact action: *Aphis craccivora*

Bean plants (*Vicia faba*) grown in pots are each infested before commencement of the test with about 200 individuals of the *Aphis craccivora* species. The plants treated in this manner are sprayed dripping wet 24 hours later with aqueous preparations containing 50, 12.5 and 3 ppm, respectively, of the compound to be tested. Two plants are used per test compound and per concentration, and an evaluation of the mortality rate achieved is made after a further 24 hours.

Compounds according to Example 1 exhibit in the above test against *Aphis craccivora* the level of action shown in the following Table.

Biological test results

In the Table which follows are summarised test results based on the Examples given in the foregoing, the index of values with regard to the percentage mortality rate of the pests being as follows:

A: >80% mortality with 50 ppm of active substance,
B: >80% mortality with 12.5 ppm of active substance, and
C) >80% mortality with 3 ppm of active substance.

| Compound No. | Action against *Aphis craccivora* |
|---|---|
| 1.1 | D |
| 1.2 | A |
| 1.3 | B |
| 2.1 | B |
| 2.2 | A |
| 2.3 | C |
| 2.12 | B |
| 2.13 | A |

3.7. Insecticidal contact action: *Myzus persicae*

Pea seedlings about 4 cm in height grown in water are each infested before commencement of the test with about 200 individuals of the *Myzus persicae* species. The plants treated in this manner are sprayed dripping wet 24 hours later with an aqueous suspension containing 400 ppm of the compound to be tested. Two plants are used per test concentration, and an assessment of the mortality rate attained is made 48 hours after application. The test is carried out at 20°–22° C. with 60% relative humidity.

Compounds of the formula I according to Example 1 have an 80–100% action in this test.

3.8. Action against soil insects (*Diabrotica balteata*)

Five maize seedlings about one to three cm in length and also a disk of filter paper are immersed in an aqueous preparation containing 0.2 to 12.5 ppm of the active ingredient to be tested. The moist filter paper disk is laid out on the bottom of a 200 ml plastic beaker, and the 5 treated maize seedlings together with 10 larvae of *Diabrotica balteata* of the second to third larval stage are placed into the beaker. Two batches are carried out per active-ingredient concentration. The beakers infested with the larvae are kept for 6 days in daylight, with a relative humidity of 40 to 60% and at a temperature of 22° to 24° C. The percentage mortality rate of the test larvae is afterwards assessed.

Compounds according to Example 1 exhibit in this test an 80–100% action.

3.9. Action against ticks (A) *Amblyomma hebraeum*

50 nymphs are counted into a small glass test tube, and immersed for 1 to 2 minutes in 2 ml of an aqueous emulsion from a dilution series of 10, 1 or 0.1 ppm of test substance. The test tubes are then sealed with a standardised cotton plug, and inverted so that the active-substance emulsion can be absorbed by the cotton wool. The evaluation is made after 1 week. Two repeats are made for each test.

(B) *Boophilus microplus* (larvae)

With a dilution series analogous to that of Test A, tests are carried out with 20 sensitive larvea and OP-resistant larvae, respectively (resistance is with respect to diazinon compatibility).

The compounds according to the Production Example 1 exhibit an 80–100% action against nymphs and larvae of the ticks: *Amblyomma hebraeum* and *Boophilus microplus*.

3.10. Insecticidal action: *Nilaparvata lugens*

Rice plants are sprayed with a test solution containing 400 ppm of the compound to be tested. After the drying of the coating, nymphs of *Nilaparvata lugens*($N_2$ or $N_3$ stage) are settled onto the plants. There are used two plants per test compound and per test species. An assessment of the mortality rate achieved is made after 6 days. The test is carried out at 26° C. with 60% relative humidity.

Compounds according to Example 1 exhibit in the above test a 100% action against *Nilaparvata lugens* nymphs.

3.11. Systemic insecticidal action: *Nilaparvata lugens*

Rice plants are sprayed in each case with 5 ml of a test solution containing 50, 12.5 and 3 ppm, respectively, of the compound to be tested, and after 1, 2 and 3 weeks, 20 nymphs are settled onto each plant. An evaluation of the attained mortality rate is made 6 days after the infestation of the plants Compounds according to Example 1 exhibit in this test an 80–100% action.

What is claimed is:

1. A phenylhydrazine of the formula I

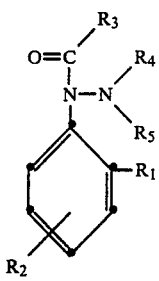

wherein
R$_1$ is —O—R—Z;
R is C$_1$–C$_4$-alkylene or —CH(CH$_2$OCH$_3$)—CH$_2$—;
Z is methoxy, ethoxy, methylthio, ethylthio, methylsulfinyl, methylsulfonyl, halogen or trifluoromethyl; or
R and Z together are

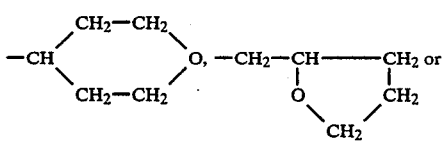

R$_2$ is hydrogen or methyl;
R$_3$ is halogen;
R$_4$ is hydrogen; R$_5$ is —CO—O—R$_6$; or
R$_3$, R$_4$ and R$_5$ together form a bridge member of the formula

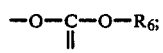

and
R$_6$ is methyl or ethyl.

2. A compound according to claim 1, wherein
R is C$_2$–C$_4$-alkylene;
Z is methoxy, ethoxy, methylthio, ethylthio, methylsulfonyl, fluorine, chlorine or triofluoromethyl; or
R and Z together are

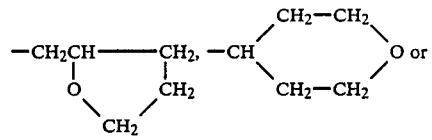

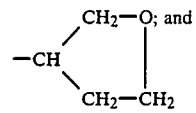

R$_6$ is methyl.

3. A compound according to claim 2 wherein
R is —CH$_2$—CH$_2$—, —CH$_2$—CH$_2$—CH$_2$— or —CH(CH$_3$)—CH$_2$—; and
R$_3$ is chlorine.

4. A compound according to claim 1, wherein R$_3$, R$_4$ and R$_5$ form a bridge member of the formula

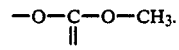

5. The compound according to claim 1 of the formula

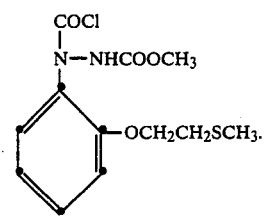

6. The compound according to claim 1 of the formula

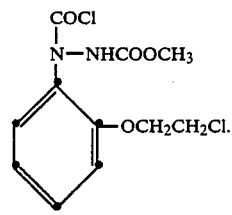

7. The compound according to claim 1 of the formula

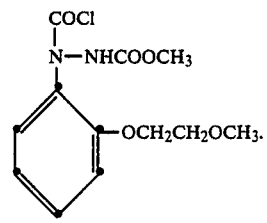

8. The compound according to claim 1 of the formula

9. The compound according to claim 1 of the formula

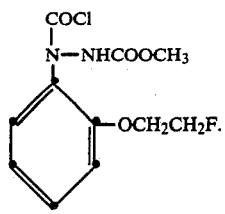

10. The compound according to claim 1 of the formula

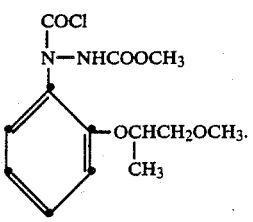

11. The compound according to claim 1 of the formula

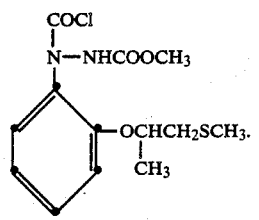

12. The compound according to claim 1 of the formula

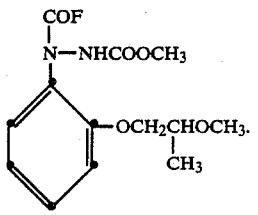

13. The compound according to claim 1 of the formula

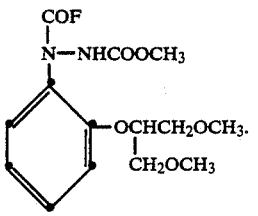

14. The compound according to claim 1 of the formula

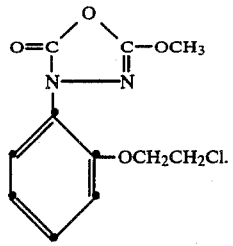

15. The compound according to claim 1 of the formula

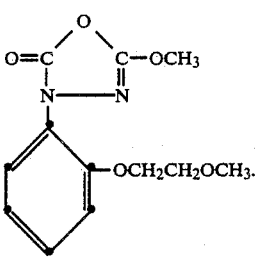

16. The compound according to claim 1 of the formula

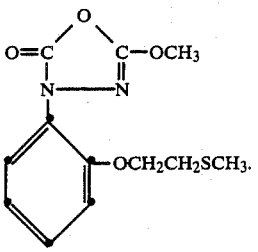

17. The compound according to claim 1 of the formula

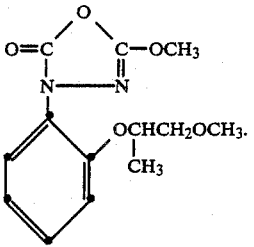

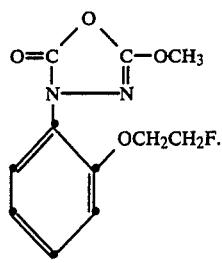

18. The compound according to claim 1 of the formula

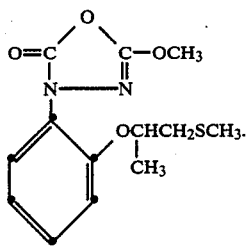

19. The compound according to claim 1 of the formula

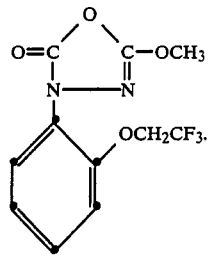

20. The compound according to claim 1 of the formula

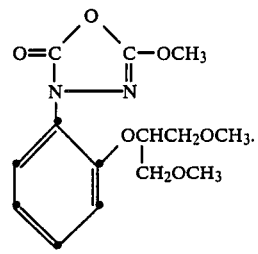

21. A pesticidal composition which comprises as active ingredient an insecticidally or acaricidally effective amount of a compound according to claim 1 in combination with a pesticidally acceptable carrier or additive.

22. A method of controlling pests selected from insects and acarides on animals and plants and in the soil, which method comprises applying thereto or to the locus thereof a pesticidally effective amount of a compound according to claim 1.

* * * * *